(12) United States Patent
Leyva

(10) Patent No.: US 10,478,748 B2
(45) Date of Patent: *Nov. 19, 2019

(54) DUAL CHANNEL CONNECTOR UNITS, DEVICES, METHODS, AND SYSTEMS INCLUDING THE SAME

(71) Applicant: SoClean, Inc., Oxford, MA (US)

(72) Inventor: Timothy Leyva, Bellingham, MA (US)

(73) Assignee: SoClean, Inc., Peterborough, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/928,287

(22) Filed: Mar. 22, 2018

(65) Prior Publication Data

US 2018/0311595 A1 Nov. 1, 2018

Related U.S. Application Data

(63) Continuation of application No. 15/498,954, filed on Apr. 27, 2017, now Pat. No. 9,962,627.

(51) Int. Cl.
*F16L 39/00* (2006.01)
*B01D 11/04* (2006.01)
(Continued)

(52) U.S. Cl.
CPC ........ *B01D 11/0403* (2013.01); *A23L 3/3409* (2013.01); *A23L 3/34095* (2013.01);
(Continued)

(58) Field of Classification Search
CPC ............ F16L 5/14; F16L 39/005; F16L 39/03
(Continued)

(56) References Cited

U.S. PATENT DOCUMENTS 4,257,748 A * 3/1981 Ives ........................ G01F 1/375
285/140.1
4,482,172 A * 11/1984 DeVera ................... F16L 39/00
285/140.1
(Continued)

FOREIGN PATENT DOCUMENTS

DE 9104578.9 8/1992
DE 9104578 U1 * 8/1992 ................ F16L 5/14
(Continued)

OTHER PUBLICATIONS

International Search Report and Written Opinion dated Jun. 4, 2018, issued in PCT Patent Application No. PCT/US2018/029133, 9 pages.
(Continued)

*Primary Examiner* — David Bochna
(74) *Attorney, Agent, or Firm* — Grossman Tucker Perreault & Pfleger PLLC

(57) ABSTRACT

Technologies for providing a gas inlet and gas outlet to a compartment are described. In embodiments, the technologies include a dual channel connector unit that includes an inlet passageway and an outlet passageway. In embodiments at least a portion of the outlet passageway is disposed radially around the inlet passageway. The connector unit is configured to install into a portion (e.g., wall, bottom, top, or lid) of a compartment. Systems and methods including such connector units are also described.

20 Claims, 14 Drawing Sheets

(51) Int. Cl.
    *B67D 7/04*     (2010.01)
    *B67D 7/32*     (2010.01)
    *A23L 3/3409*     (2006.01)
    *A61L 2/26*     (2006.01)
    *A61L 2/20*     (2006.01)

(52) U.S. Cl.
    CPC ................. *A61L 2/26* (2013.01); *B67D 7/04* (2013.01); *B67D 7/32* (2013.01); *A61L 2/202* (2013.01); *A61L 2202/123* (2013.01); *A61L 2202/13* (2013.01); *B67D 2007/0426* (2013.01); *B67D 2007/0428* (2013.01); *F16L 39/005* (2013.01)

(58) Field of Classification Search
    USPC .................... 285/40, 18, 141.1, 140.1, 143.1
    See application file for complete search history.

(56) References Cited

U.S. PATENT DOCUMENTS

| | | | | |
|---|---|---|---|---|
| 4,762,343 | A * | 8/1988 | Hirohata | F16L 5/12 285/140.1 |
| 4,922,971 | A * | 5/1990 | Grantham | F16L 39/005 285/123.15 |
| 5,683,576 | A | 11/1997 | Olsen | |
| 6,074,565 | A | 6/2000 | Buckner | |
| 6,609,733 | B2 * | 8/2003 | Gilmore | B01F 5/0451 285/143.1 |
| 7,240,700 | B2 * | 7/2007 | Pangallo | B62D 25/24 285/140.1 |
| 7,472,929 | B2 * | 1/2009 | Fattorusso | F16L 31/00 285/140.1 |
| 7,491,321 | B1 | 2/2009 | Maas et al. | |
| 7,767,168 | B2 | 8/2010 | Namespetra et al. | |
| 8,298,492 | B2 | 10/2012 | Shiotani et al. | |
| 9,956,309 | B1 | 5/2018 | Leyva | |
| 9,986,871 | B1 | 6/2018 | Leyva | |
| 10,264,913 | B2 | 4/2019 | Leyva | |
| 10,322,199 | B2 | 6/2019 | Leyva | |
| 2003/0049164 | A1 | 3/2003 | Bon et al. | |
| 2004/0051308 | A1 * | 3/2004 | Coates | F16L 39/005 285/124.1 |
| 2009/0039033 | A1 | 2/2009 | Kee et al. | |
| 2010/0170857 | A1 | 7/2010 | Williams et al. | |
| 2014/0154134 | A1 | 6/2014 | Leyva | |
| 2015/0050194 | A1 | 2/2015 | Li | |
| 2016/0102785 | A1 * | 4/2016 | Bibbo | F16L 5/02 285/141.1 |
| 2016/0242596 | A1 | 8/2016 | Bennett | |
| 2018/0310756 | A1 | 11/2018 | Leyva | |

FOREIGN PATENT DOCUMENTS

| | | | |
|---|---|---|---|
| FR | 1529814 | 5/1968 | |
| FR | 1529814 A * | 6/1968 | ............ F16L 39/005 |
| GB | 658755 | 10/1951 | |
| GB | 658755 A * | 10/1951 | ............ F16L 39/005 |
| WO | 2018200500 | 11/2018 | |
| WO | 2018200504 | 11/2018 | |
| WO | 2018200514 | 11/2018 | |
| WO | 2018200519 | 11/2018 | |

OTHER PUBLICATIONS

International Search Report and Written Opinion dated Jul. 13, 2018, issued in PCT Patent Application No. PCT/US2018/029115, 12 pages.
Office Action dated Jul. 13 2018, issued in U.S. Appl. No. 15/969,427, 7 pages.
International Search Report and Written Opinion dated Jul. 19, 2018, issued in PCT Patent Application No. PCT/US2018/029111, 13 pages.
Office Action dated Aug. 23, 2017, issued in U.S. Appl. No. 15/498,884, 8 pages.
Office Action dated Aug. 23, 2017, issued in U.S. Appl. No. 15/499,070, 8 pages.
Office Action dated Aug. 30, 2017, issued in U.S. Appl. No. 15/498,954, 7 pages.
Notice of Allowance dated Dec. 14, 2017, issued in U.S. Appl. No. 15/499,070, 5 pages.
Notice of Allowance dated Dec. 18, 2017, issued in U.S. Appl. No. 15/498,954 5 pages.
Notice of Allowance dated Feb. 7, 2018, issued in U.S. Appl. No. 15/498,884, 5 pages.
Office Action dated May 15, 2018, issued in U.S. Appl. No. 15/919,833, 8 pages.
International Search Report and Written Opinion dated May 21, 2018, issued in PCT Patent Application No. PCT/US2018/029127, 7 pages.
Office Action dated Oct. 29, 2018, issued in U.S. Appl. No. 15/499,167, 9 pages.
Office Action dated Oct. 29, 2018, issued in U.S. Appl. No. 15/919,833, 9 pages.
Notice of Allowance dated Dec. 12, 2018, issued in U.S. Appl. No. 15/969,427, 5 pages.
Notice of Allowance dated Feb. 4, 2019, issued in U.S. Appl. No. 15/919,833, 6 pages.

* cited by examiner

DUAL CHANNEL CONNECTOR UNITS, DEVICES, METHODS, AND SYSTEMS INCLUDING THE SAME

CROSS-REFERENCE TO RELATED APPLICATION

This application is a continuation of U.S. patent application Ser. No. 15/498,954 (now U.S. Pat. No. 9,962,627) filed Apr. 27, 2017, the entire content of which is incorporated herein by reference.

FIELD

The present disclosure generally relates to connector units for providing a gas inlet and gas outlet. In particular, the present disclosure relates to a double walled connector unit, wherein a first wall forms a first passageway and a second wall extends radially from the first wall to form a second passageway, such that a gas inlet passageway and a gas outlet passageway are housed within a single connector unit. Devices, systems and methods utilizing the connector unit are also described.

BACKGROUND

The safe transfer of one or more gases between components of a system is important for many industrial and consumer applications. Indeed, many useful industrial gases are harmful to the environment and human health and, thus, need to be contained during their transfer to prevent unintended exposure to humans and/or the environment. Appropriate exhaustion and/or treatment of such gases may also be needed.

A wide variety of gas transfer fittings are known. In many instances, such fittings include tight fitting seals and/or gas tight valves, wherein a separate fitting is used to provide a gas inlet and a gas outlet. However, the inventors have identified that there is a need for technologies that provide a gas inlet and outlet within a single gas fitting, i.e., a single connector unit, device, insert or the like. In particular, the inventors have identified that there is a need in the art for technologies for providing a gas inlet and outlet for the provision and removal of a sanitizing gas from a container.

BRIEF DESCRIPTION OF THE DRAWINGS

Reference is now made to the following detailed description which should be read in conjunction with the following figures, wherein like numerals represent like parts.

DETAILED DESCRIPTION

Figure 1:
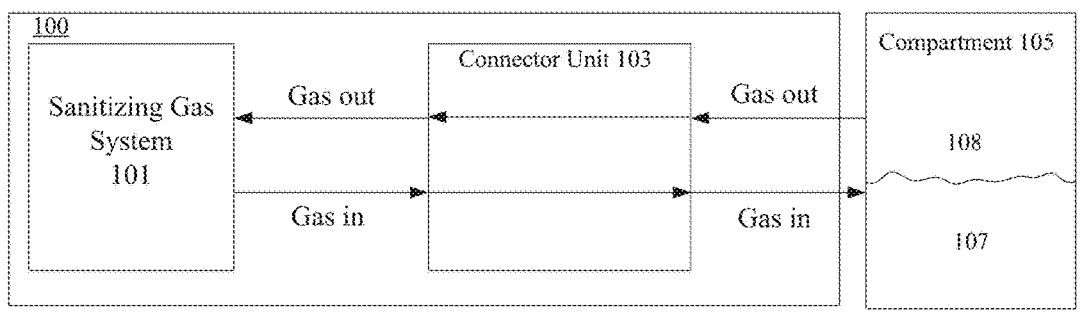
FIG. 1 is a block diagram illustrating gas flow between a compartment sanitization system, a dual channel connector unit, and a compartment.

Aspects of the present disclosure relate to technologies (e.g., devices, systems, and methods) for providing a gas inlet for introducing a gas and a gas outlet for removing a gas. In particular, the technologies described herein relate to connector units that include both a gas inlet and a gas outlet. In embodiments, the connector units described herein include gas inlet channel and a gas outlet channel, wherein at least a portion of the gas outlet channel is disposed radially around the gas inlet channel. The connector units described herein are particularly useful in sanitizing applications, e.g., where a sanitizing gas such as ozone is used to sanitize a container within which the connector unit is installed.

For the sake of illustration the present disclosure describes various example embodiments in which a connector unit is used to provide a gas inlet for the provision of a sanitizing gas to a container such as a water reservoir and a gas outlet for the removal of excess or unused sanitizing gas from the container. It should be understood that such examples are for the sake of illustration only, and that the technologies described herein may be used to sanitize a wide variety of compartments.

Although the technologies described herein can be used with many gases, the present disclosure focuses on the use of ozone as a sanitizing gas. Ozone is an effective sanitization agent, is relatively easy to generate on site (and thus does not require the use of a storage tank), and leaves little or no chemical residue. For those and other reasons, ozone has been identified as a safe and effective for use as a sanitizing gas with the connector units described herein. Again, however, the connector units of the present disclosure may be used with any suitable gas.

As used herein, the term "fluidly coupled" means that two or more components are connected to one another such that a gas may be conveyed between them. In contrast, the term "coupled" when used alone means that two or more components are connected to one another chemically (e.g., via an adhesive), mechanically (e.g., via fasteners, mechanical interference, etc.), or by other means.

One aspect of the present disclosure relates to dual channel connector units that are useful for providing a gas inlet to and a gas outlet from a compartment. As will be described further below, the dual channel connector units (also referred to herein as simply a "connector unit") described herein include an inlet passageway (channel) and an outlet passageway (channel), wherein the inlet passageway has a first proximal end and a first distal end, and the outlet passageway includes a second proximal end and a second distal end. The dual channel connector units described herein are configured to be installed within a portion of a compartment, such as but not limited to a wall, cover, or bottom thereof. When so installed, the connector unit spans through a thickness of the portion of the compartment, such that the first and second distal ends are within an interior of the compartment, and the first and second proximal ends are outside the compartment.

In embodiments, the dual channel connector units described herein are configured such that at least a portion of the outlet passageway is disposed radially around the inlet passageway. The gas supply system is configured to generate a sanitizing gas (e.g., ozone) and to fluidly couple to the first proximal end, such that sanitizing gas is conveyed through the inlet passageway into an interior of the compartment. The exhaust system is configured to couple to the second proximal end, and to draw sanitizing gas (e.g. ozone) from the interior of the compartment through the outlet passageway via the second distal end. In embodiments, the exhaust system includes a filter for converting or destroying the sanitizing gas removed from the interior of the compartment.

FIG. 1 is a block diagram illustrating sanitizing gas flow between a compartment sanitization system, a dual channel connector unit, and a compartment. As shown, the compartment sanitization system 100 includes a sanitizing gas system 101 and a connector unit 103. The sanitizing gas system 101 is fluidly coupled to the connector unit 103 such that it can provide a gas inflow (gas in) to the connector unit 103 and receive a gas outflow (gas out) from the connector unit 103. The connector unit 103 is fluidly coupled to a compartment 105, which in this case includes a liquid (e.g., water) 107. As shown, the sanitizing gas system 101 may supply an inflow of sanitizing gas (gas in) such as ozone to the connector unit 103. The inflow of sanitizing gas passes through the connector unit 103 into the compartment 105. More particularly, in embodiments the inflow of sanitizing gas is conveyed from the connector unit 103 to beneath a surface of the liquid 107 in the compartment 107, as shown in FIG. 1.

At least a portion of the sanitizing gas supplied by the gas inflow may sanitize the liquid 107 (if any), as well as portions of the compartment that are below the level of the liquid 107. In addition, at least a portion of the sanitizing gas supplied by the gas inflow may evolve from the liquid into the air 108 within the compartment 105 and sanitize the portion of the compartment 105 that is above the level of the liquid 107. Excess sanitizing gas within the compartment 105 may be converted to another composition and/or be removed from the interior of the compartment 105 via a gas outflow (gas out) through connector unit 103. More specifically, excess sanitizing gas may be conveyed via the gas outflow through the connector unit 103 and back to the sanitization gas system 101, as shown. In embodiments, the sanitizing gas system may be configured to remove the sanitizing gas and/or convert the excess sanitizing gas to another composition.

Figure 2:
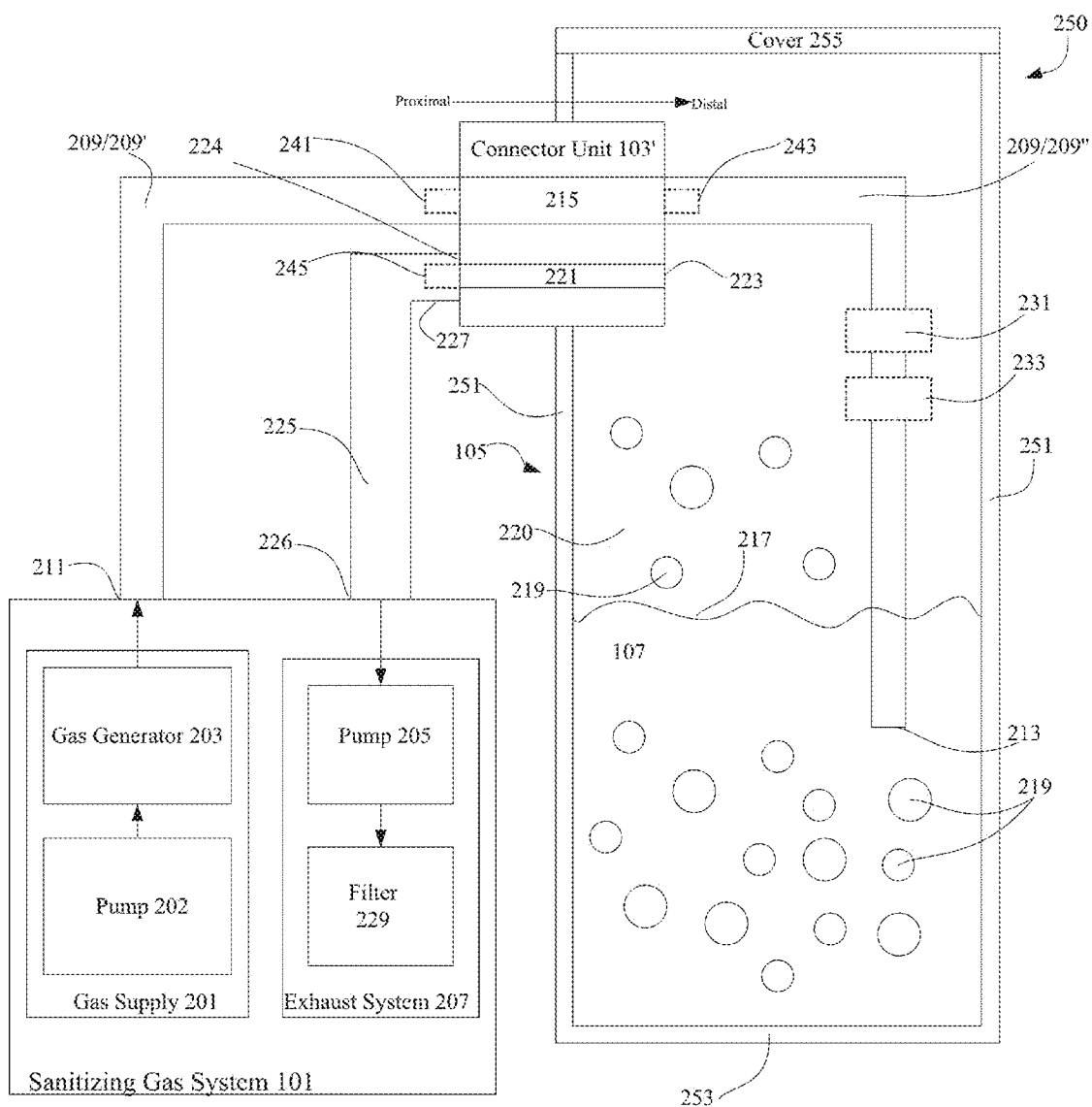
FIG. 2 is a block diagram of one example of a compartment sanitization system consistent the present disclosure.

Reference is now made to FIG. 2, which is a block diagram of one example of a compartment sanitization system 200 that includes a dual channel connector unit consistent with the present disclosure. As shown, the compartment sanitization system includes a sanitizing gas system 101 that is fluidly coupled to a dual channel connector unit 103'. In this embodiment, the sanitizing gas system 101 includes a gas supply 201 including a pump 202 and a gas generator 203. The gas generator 203 is configured to generate a sanitizing gas, such as ozone or another sanitizing gas. The pump 202 (e.g., an air pump) is configured to generate a flow of air to convey the sanitizing gas to a proximal end 211 of supply line 209.

The (dual channel) connector unit 103' includes an inlet passageway 215 and an outlet passageway 221, wherein the inlet passageway includes first proximal and distal ends, and the outlet passageway includes second proximal and distal ends. The connector unit 103' is generally configured to be installed within a portion of a compartment, such as but not limited to a wall, bottom, top, or cover of a compartment. When so installed, the connector unit 103' may span through a thickness of a portion of a compartment, such that the first and second distal ends (of the inlet and outlet passageways 215, 221 respectively) are disposed within the interior of the compartment, whereas the first and second proximal ends (of the inlet and outlet passageways) are disposed outside the compartment.

That concept is shown in the embodiment of FIG. 2, which illustrates the connector unit 103' as being installed within a wall 251 of a compartment 250, such that the distal ends (not labeled) of the inlet and outlet passageways 215, 221 are disposed within an interior of a compartment 250, and the proximal ends (not labeled) of the inlet and outlet passageways (215, 221) are disposed outside the wall 251. As further shown, the compartment may further include a bottom 253 and a cover 255, either of which may be acceptable locations for the installation of connector unit 103'.

As further shown in FIG. 2, the sanitizing gas system 101 (and, more particularly, the gas supply 201) is fluidly coupled to the connector unit 103' and/or the interior of the compartment 250 via a supply line 209. In some embodiments the supply line 209 is configured to pass through the inlet passageway 215, such that a distal end 213 of the supply line is disposed within the interior of the compartment 250. In some embodiments and as shown in FIG. 2, the distal end 213 may be located below a surface 217 of liquid 107 that may be within the compartment 250.

Alternatively in some embodiments first and second supply lines 209', 209" may be used instead of a single supply line 209. In such instances, the first supply line 209' may fluidly couple gas supply 201 with the first proximal end of the inlet passageway 215, and a proximal end of the second supply line 209" may be fluidly coupled to the first distal end of the inlet passageway 215. Coupling of the first and second supply lines 209', 209" to the inlet passageway 215 may be facilitated by optional first and second inlet connectors 241, 243, which are integral with or otherwise fluidly coupled to the first proximal and distal ends of the inlet passageway 215.

An optional check valve 231 may be provided on a distal portion of supply line 209 or on second supply line 209". When used, the optional check valve is generally configured to prevent a backflow of liquid 107 into the supply line 209 (or first and second supply lines 209', 209"). An optional sensor 233 may also be provided to sense a presence and/or concentration of sanitizing gas (e.g. ozone gas) within the interior of compartment 250 and/or within connector unit 103'. In some embodiments the sensor 233 (when used) may be configure to provide a signal to a user interface, wherein the signal causes the user interface to indicate whether or not a safe level of the sanitizing gas is present in the compartment 250, and/or to indicate when a the compartment is safe to use.

The sanitizing gas system 101 further includes an exhaust system 207, which is fluidly coupled to a proximal end 224 of the outlet passageway 221 in the connector unit 103', in this case via a return line 225. The exhaust system includes a pump 205 and a filter 229. As shown, the return line 225 includes a proximal end 226 fluidly coupled to the exhaust system 207 (or, more particularly, to pump 205), and a distal end 227 coupled to the proximal end 224 of the outlet passageway 221. Coupling of the distal end 227 of the return line 225 to the proximal end of the outlet passageway 221 may be facilitated by an optional outlet connector 245 that is integral with or otherwise fluidly coupled to the proximal end of the outlet passageway 221.

In operation, gas generator 203 may generate a sanitizing gas 219 (e.g., ozone). Pump 202 (e.g., an air pump) may generate a flow of air to convey a sanitizing gas 219 into the supply line 209 (or first supply line 209', when used). In instances where a single supply line 209 is used, the sanitizing gas may 219 may flow through the supply line 209 such that it passes through the inlet passageway 215 and into the interior of the compartment 250. Alternatively where first and second supply lines 209', 209" are used, the sanitizing gas 219 may flow through the first supply line 209', into the inlet passageway 215, and then into the second supply line 209". In either case, the sanitizing gas 219 may exit the distal end 213 of the supply line 209 (or second supply line 209").

When the distal end 213 is disposed beneath a surface 217 of a liquid 107 within the compartment 250, the sanitizing gas 219 may be introduced into liquid 107. In such instances a portion of the sanitizing gas 219 may sanitize the liquid 107 and the portions of compartment 250 that are below surface 217. In addition, at least a portion of the sanitizing gas 219 may evolve from the liquid 107 into the air 220 within the compartment 250, whereupon the sanitizing gas 219 may sanitize the air 220 and the interior surfaces of the walls 251 and cover 255. Likewise in instances where the distal end 213 is be disposed above surface 217, and/or no liquid 107 may be present within compartment 250, the sanitizing gas 219 may sanitizing the air and exposed surfaces of the walls 251, cover 255, and bottom 253.

During the sanitization of compartment 250, all or a portion of the sanitizing gas 219 may be converted to another composition. For example in instances where the sanitizing gas is ozone, all or a portion of the ozone may be converted to oxygen during the sanitization of the compartment 250. However, excess sanitizing gas 219 may be present within the air 220, and may need to be removed in order for the compartment to be safely used. In that regard, pump 205 (e.g., a vacuum pump) may be configured to draw excess sanitizing gas 219 from the air 220 into the distal end 223, through the outlet passageway 221, and through the return line 114. In that regard, the distal end 223 may be or include an opening that is fluidly coupled to (or configured to be fluidly coupled to) the interior of the compartment 250. Sanitizing gas 219 removed from the interior of the compartment 250 by the pump 205 may be conveyed to the filter 229.

The filter 229 may be configured to remove all or a portion of the sanitizing gas 219 conveyed thereto. For example, filter 229 may be configured to absorb at least a portion of the sanitizing gas 219. Alternatively or additionally, the filter 229 may be configured to convert the sanitizing gas to another composition, such as a composition that is acceptable for human inhalation and/or exhaust into the environment. In instances where the sanitizing gas 219 is ozone, for example, the filter 229 may be configured to convert all or a portion of the sanitizing gas to oxygen. Non-limiting examples of suitable filters that may be used as filter 229 include activated carbon filters, magnesium oxide filters, combinations thereof, and the like.

For the sake of clarity and ease of understanding, it is noted that FIG. 2 depicts a compartment 250 in combination with the compartment sanitization system 200, but it should be understood that the compartment sanitization systems described herein need not include the compartment. Indeed, the systems described herein may be used with suitable compartment, and are not limited to use with compartments consistent with those illustrated in the figures.

It is noted that FIG. 2 depicts the use of a (dual channel) connector unit 103' that includes inlet and outlet passageways 215/2211 that are laterally offset from one another. It should be understood that such illustration is for the sake of example only, and that other connector units may be used in the technologies of the present disclosure. Indeed as will be described later in connection with FIGS. 3-6B, the technologies described herein may include and/or utilize a dual channel connector unit that includes an inlet passageway and an outlet passageway, wherein at least a portion of the outlet passageway is disposed radially around the inlet passageway. For ease of reference, such connector units may be referred to herein as a "double wall connector unit."

Figure 3:
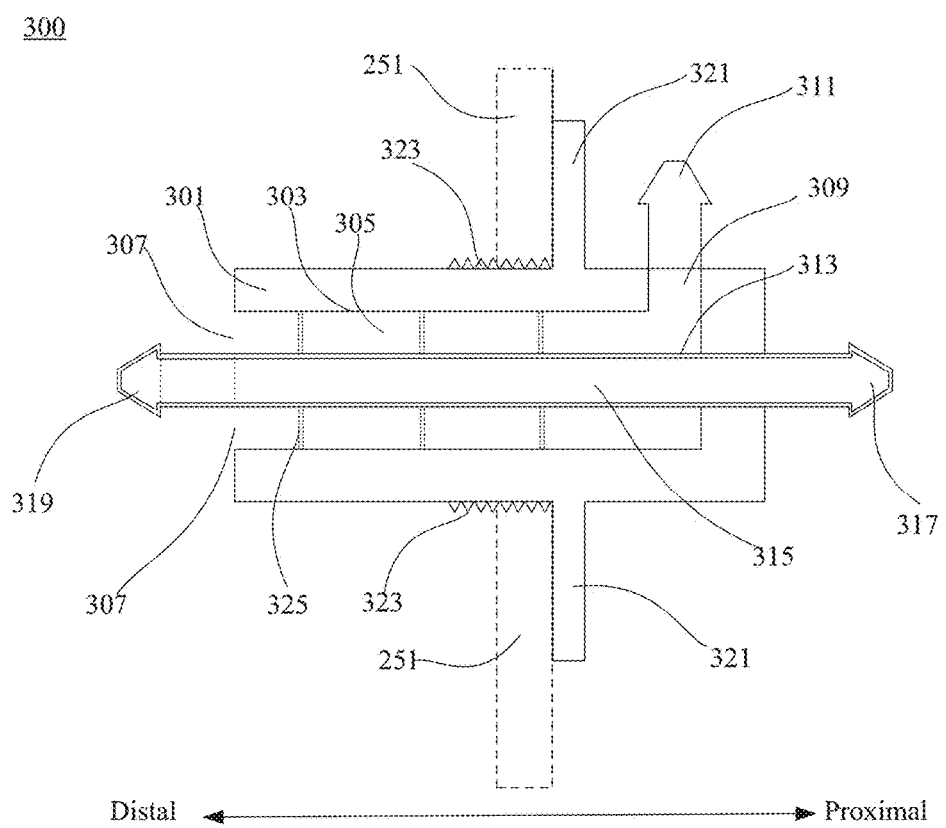
FIG. 3 is a cross sectional view of one example of a double wall connector unit consistent with the present disclosure.

FIG. 3 is a cross sectional diagram of one example of a double wall connector unit consistent with the present disclosure. As shown, double wall connector unit 300 includes an outer wall 301 and an inner wall 313, both of which are tubular or cylindrical in shape. An inlet passageway 315 is defined in the inner wall 313 and extends from a first inlet connector 317 to a second inlet connector 319. The outer wall 301 includes an inner surface 303 and the inner wall 313 has an outer surface 314. An outlet passageway 305 is defined between the inner surface 303 and the outer surface 314. Thus, at least a portion of the outlet passageway 305 is disposed radially around the inlet passageway 315.

The outlet passageway extends from an opening 307 at a distal end thereof to an outlet connector 311, which is disposed near a proximal end of the connector unit 300. In some embodiments, optional spacer elements 325 may be disposed between the inner wall 313 and the outer wall 301. When used, the optional spacer elements 325 may be configured to maintain a gap forming a portion of the outlet passageway between the inner wall 313 and the outer 301.

The double wall connector unit 300 further includes a flange 321 and coupling elements 323. In general, the coupling elements 323 are configured to facilitate the installation of the double wall connector unit 300 into a portion of a compartment. To illustrate that concept, FIG. 3 depicts double wall connector unit as installed into a wall 251 of a compartment. In the illustrated embodiment, coupling elements 323 are configured as teeth, threads, or other mechanical coupling elements that engage with an inward facing surface of an opening (not shown) in the wall 251.

In some embodiments, the coupling elements 323 may be self-tapping threads that are configured to form and threadably engage with threads in an inward facing surface of the wall 251 or another portion of a compartment. For example, following the provision of an unthreaded pilot hole in wall 251, distal end of the double wall connector unit 300 may be inserted into the pilot hole. During such insertion, the double wall connector unit 300 may be rotated about an axis extending through and parallel with the inlet passageway 317. During such rotation the coupling elements 323 (e.g., self-tapping threads) may engage the inward facing surface of the pilot hole and form corresponding threads therein as the double wall connector unit 300 is advanced therein. Advancement of the double wall connector unit 300 may continue until a distal surface of the flange 321 contacts a portion of the wall 251 about the hole, at which time the double wall connector unit 300 may be considered to be in an installed position.

Of course, use of self-tapping threads and an unthreaded pilot hole is not required. For example, in some embodiments a pre-threaded pilot hole may be provisioned in wall 251. In such instances, the distal end of the double wall connector unit 300 may be inserted in the pre-threaded hole. The double wall connector unit may then be rotated to threadably engage the coupling elements 323 with the threads of the pre-threaded hole, so as to advance the distal end of the double wall connector unit 300 until the distal surface of the flange 321 contacts a portion of the wall 251 about the pre-threaded hole.

While the embodiment of FIG. 3 is useful (particularly in instances where a double wall connector unit is to be installed by a manufacturer of a compartment), consumers may be unable to provide a pilot hole in a compartment, or may find it inconvenient to do so. Accordingly, (dual channel) connector units that are capable of forming their own hole in a portion of a compartment own may be desired. Such connector units are referred to herein as a "self-drilling connector unit." It is noted that the term "self-drilling" is used herein to refer to the general capability of a connector unit to form a hole in a portion (e.g., wall, bottom, top, or lid) of a compartment, but is not used to limit the manner in which that hole is formed. Thus while in some embodiments the self-drilling connector units described herein may be configured to form a hole in a compartment by "drilling," they are not limited to such modalities. For example, the self-drilling connector units may be configured to form a hole in a compartment by cutting, drilling, punching, coring, combinations thereof, and the like.

Figure 4A:
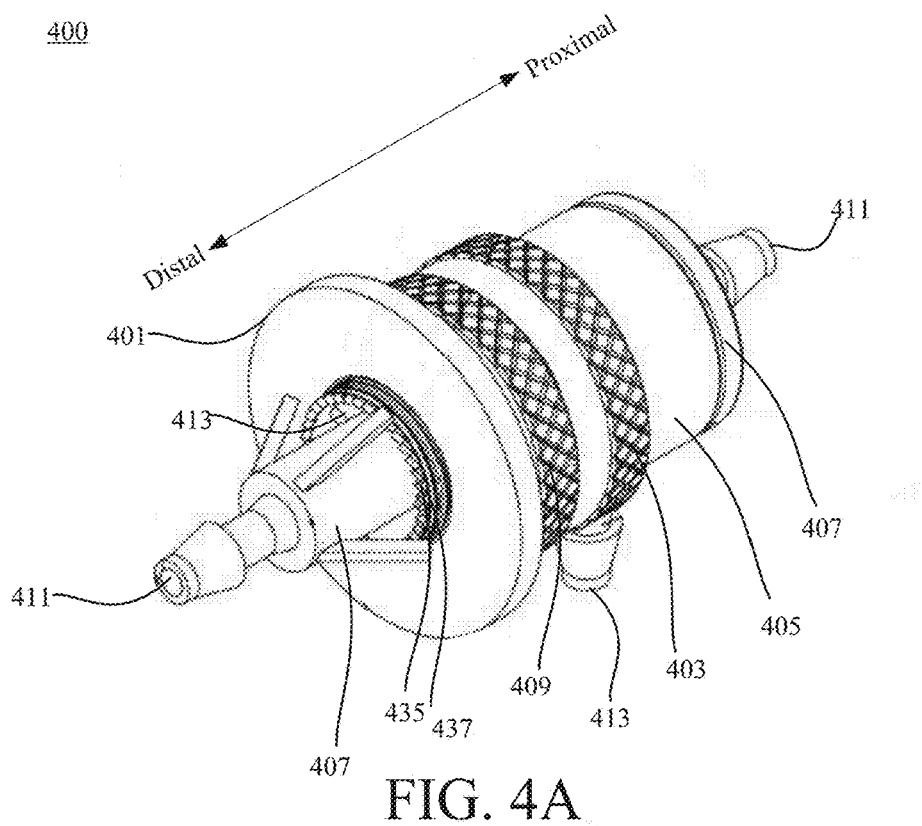
FIG. 4A is a perspective view of another example of a double wall connector unit consistent with the present disclosure.
Figure 4B:
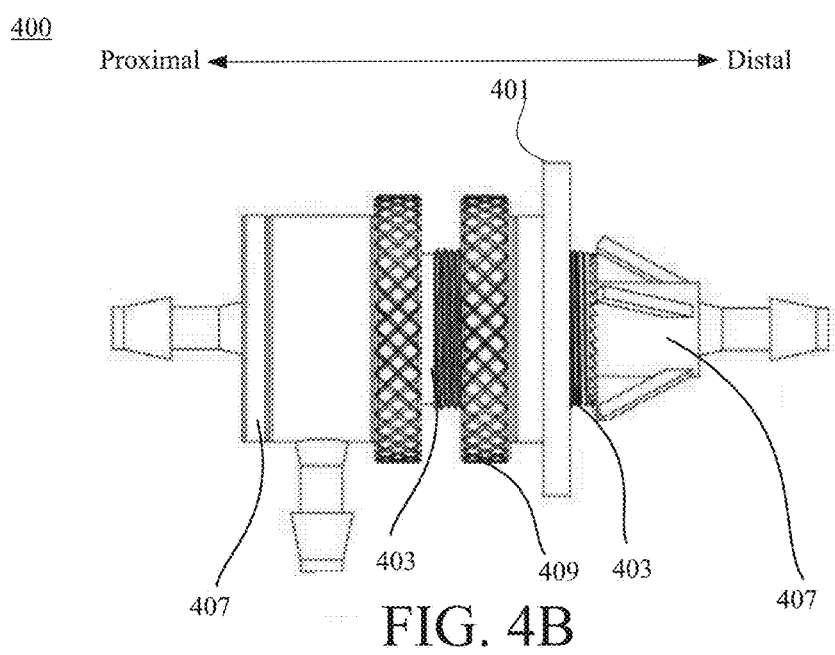
FIG. 4B is a front view of the double wall connector unit of FIG. 4A.
Figure 4C:
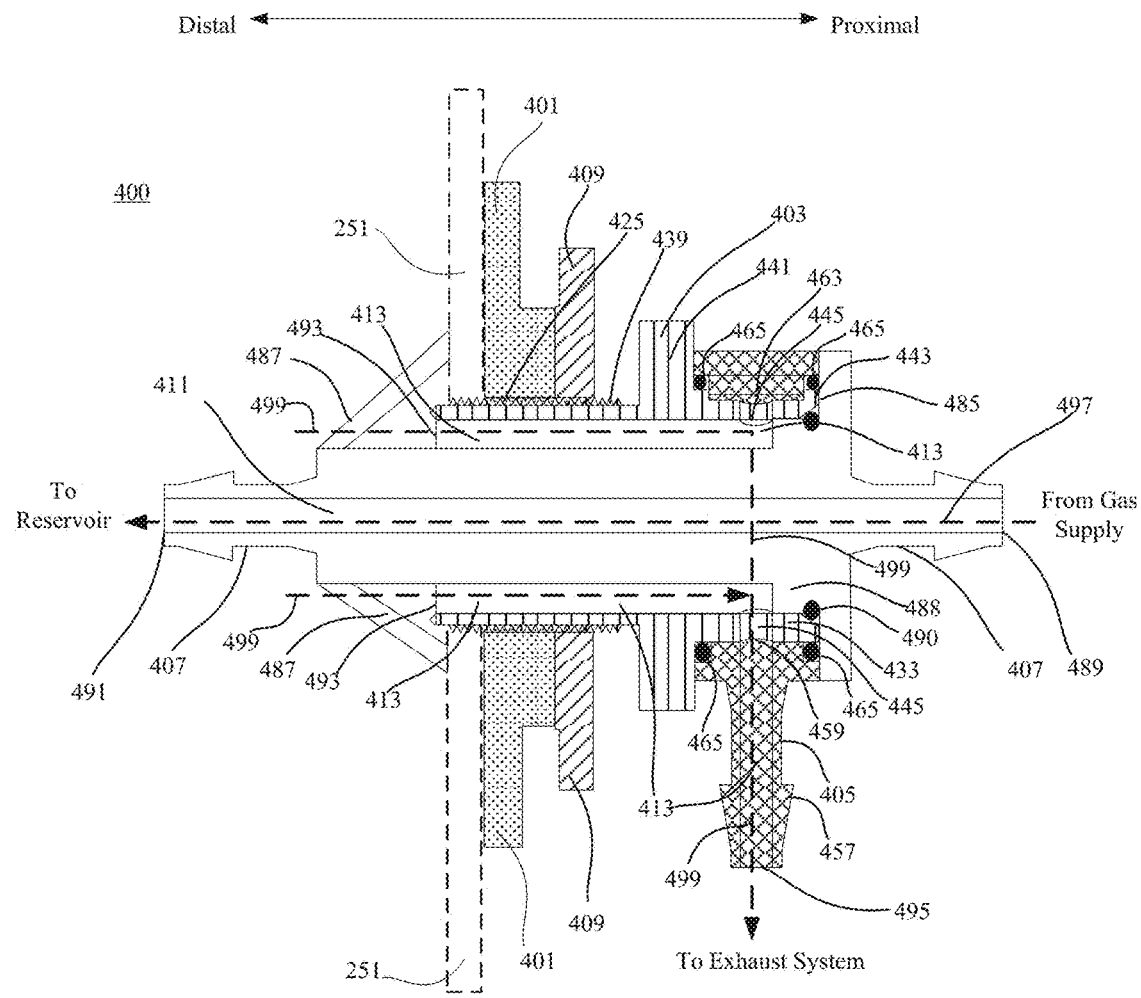
FIG. 4C is a cross-sectional view of the double wall connector unit of FIG. 4A.
Figure 4D:
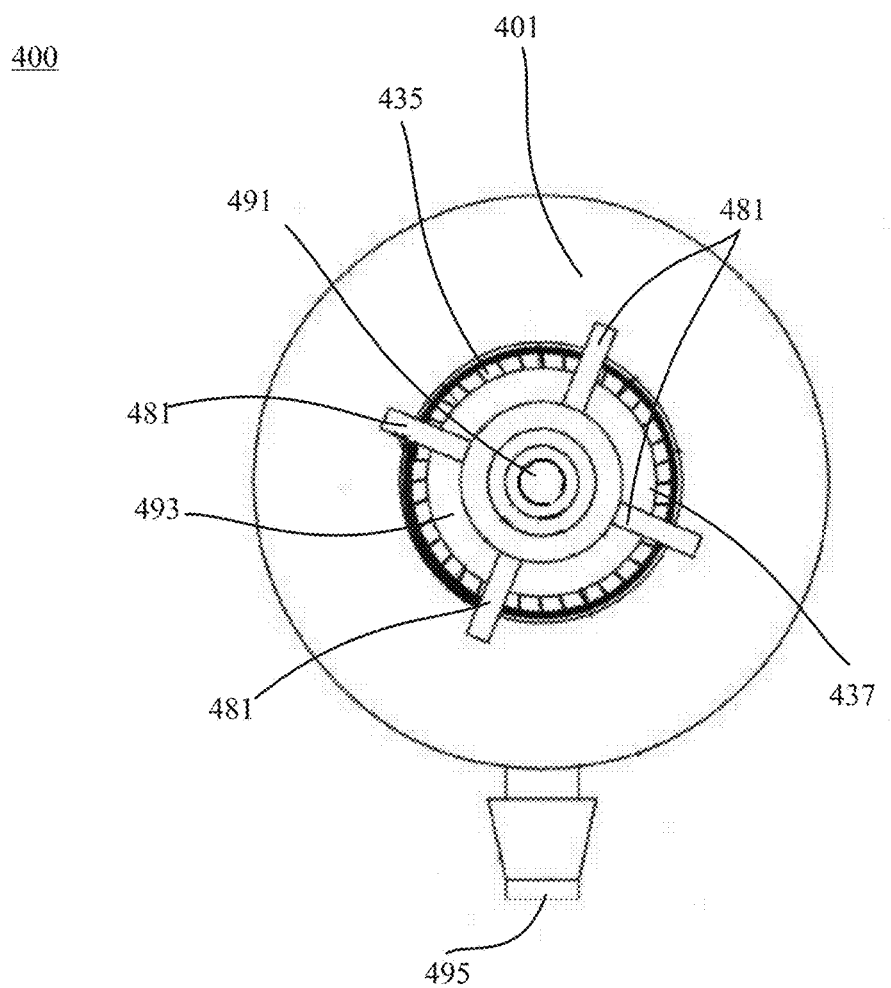
FIG. 4D is a front view of the double wall connector unit of FIG. 4A.
Figure 4E:
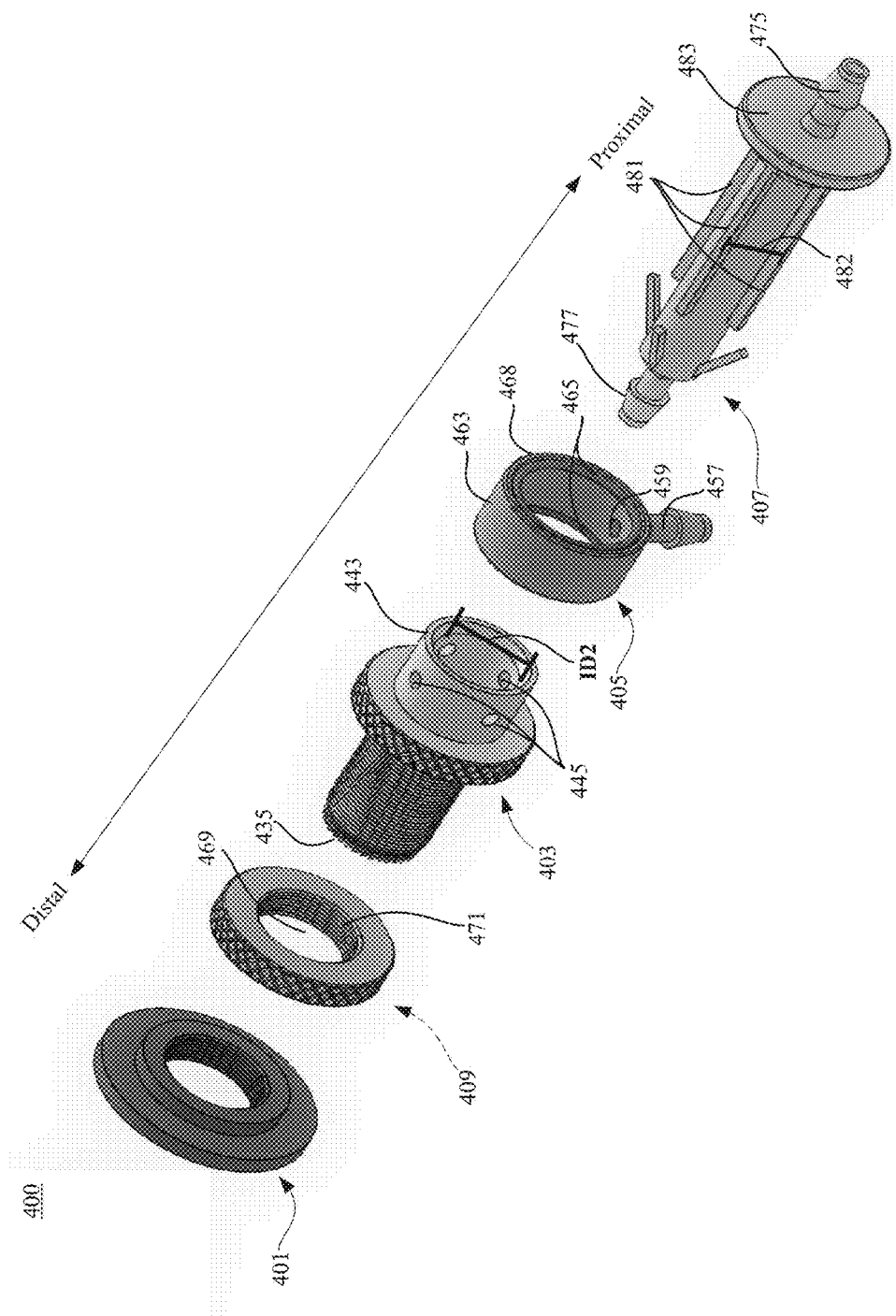
FIG. 4E is an exploded perspective view of the double wall connector unit of FIG. 4A.

FIGS. 4A-4K depict various views of one example of a self-drilling (dual channel) double wall connector unit 400 (hereinafter, connector unit 400) consistent with the present disclosure, as well as components thereof. As best shown in FIG. 4E, connector unit 400 includes a first connector portion 401, a second connector portion 403, a third connector portion 405, a fourth connector portion 407, and an optional locking element 409. As will be described in detail below such components of connector unit 400 are configured to provide an inlet passageway for the provision of a sanitizing gas into a compartment, and an outlet passageway for the removal of the sanitizing gas from the compartment. In addition, the connector unit 400 is configured such that it forms, during installation, a hole in a portion of a compartment.

Figure 4F:
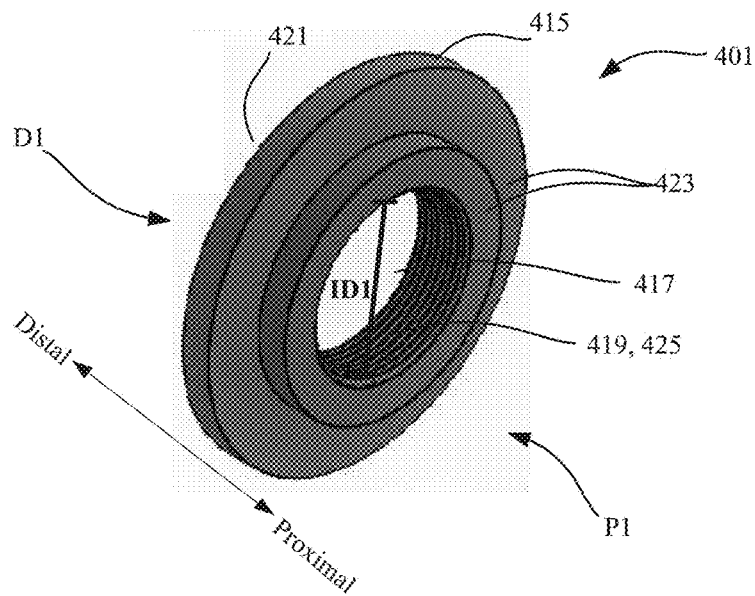
FIG. 4F is a perspective view of a first connector portion consistent with the present disclosure.

As best shown in FIG. 4F, the first connector portion 401 includes a first (e.g., tubular, circular or cylindrical) body 415 having a proximal end P1 and a distal end D1. An opening 417 is defined at least in part by an inner surface 419 of a wall of the first body 415 and extends from the proximal end P1 to the distal end D1. In general, the first connector portion 401 is configured to couple or be coupled to a wall (e.g., wall 251) or another portion of a compartment, e.g., via an adhesive, tape, mechanical fasteners, ozone resistant adhesives such a silicone or acrylic glue, or some other means (not shown).

In some embodiments the first connector portion 401 includes an inward facing surface 421 and an outward facing surface 423. The inward facing surface 421 is configured to face toward a portion of a compartment, such as but not limited to wall 251 when the first connector portion 401 is coupled thereto. In contrast, the outward facing surface 423 is configured to face away from the (e.g., wall of) compartment. Although not shown, the first connector portion 401 may also include a first sealing element that is configured to be disposed between the inward facing surface 421 and a wall of a compartment. When used, the first sealing element may be configured to form a liquid and/or gas tight seal between the first connector portion 401 and a wall of the compartment when the first connector portion 421 is urged against that wall. One example of a suitable first sealing element is an O-ring seal, which may be at least partially disposed within a groove (not shown) in the inward facing surface 421 of the first connector portion that is formed around the opening 417.

The opening 417 may include first guide elements 425 therein. The first guide elements 425 are generally configured to guide at least a portion of the second connector portion 403 when it is inserted into the opening 417. For example and as shown in FIG. 4F, the first guide elements 425 may be internal female threads formed in at least a portion of the inner surface 419. In such instances the first guide elements 425 may be configured to threadably couple with corresponding second guide elements 439 (e.g., outer male threads) on the second connector portion 403, as best shown in FIG. 4C. More specifically, the first guide elements 425 may be configured to threadably engage second guide elements 439 of the second connector portion 403, thereby coupling the first connector portion 401 to the second connector portion 403 and drawing the second connector portion 403 into the opening 417.

Figure 4G:
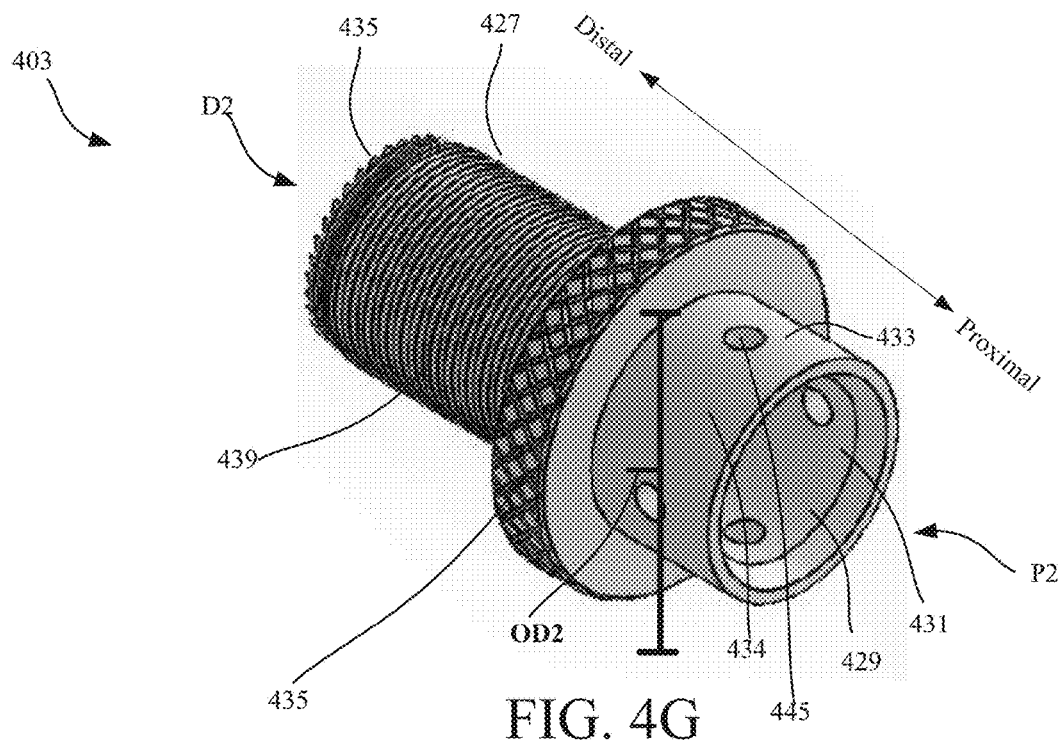
FIG. 4G is a perspective view of a second connector portion consistent with the present disclosure.

As best shown in FIGS. 4A, 4E, and 4G, the second connector portion 403 includes a second (e.g., tubular, circular or cylindrical) body 427 that has a proximal end P2 and a distal end D2. A first passageway 429 is defined at least in part by an inner surface 429 of a wall 433 of the second body 427, and extends from the proximal end P2 to the distal end D2 of the second body 427. Self-drilling elements 435 may be coupled to or integral with at least a portion of the distal end D2/edge of the second body 427, as best shown in FIGS. 4A, 4D, 4E, and 4F. For example and as best shown in FIG. 4A, the distal end D2 of the second body 427 may include a circumferential edge 437 that extends around the distal end D2 of the first passageway 429 (and, hence, outlet passageway 413), wherein self-drilling elements 435 (e.g., cutting/drilling/abrading teeth, blades, surfaces, etc.) may be disposed on or integral with a facing surface of the circumferential edge 437.

At least a portion of the second body 427 is configured to be disposed within the opening 417 of the first connector portion 401. In that regard at least a portion of the opening 417 of the first connector portion 401 may have an inside diameter ID1 that is larger than an outside diameter OD2 of at least a portion of the second body 427. As a result, at least a portion of the second body 427 may be inserted into the opening 417 of the of the first connector portion 401.

Second guide elements 439 (e.g., male threads) may be disposed on or integral with a portion of an outer surface of the second body 427. The second guide elements 439 are generally configured to interact with the first guide elements 425 of the first connector portion 401, as best shown in FIG. 4C. In that manner, the first and second guide elements 425, 439 may guide and urge the self-drilling elements 435 into contact with a wall (e.g., wall 251) or another portion of a compartment.

For example when the first and second guide elements 425, 439 are female and male threads, respectively, the second connector portion 403 may be configured such that when the distal end D2 is inserted into the opening 417 and the second connector portion 403 is rotated, the second guide elements 439 threadably engage with the first guide elements 425 so as to draw the distal end D2 into the opening 417 and ultimately into contact with a portion (e.g., wall 251) of a compartment. Further rotation of the second connector portion 403 may cause the self-drilling elements 435 to form a hole in a portion (e.g., wall 251) of the compartment, wherein the hole has an inward facing surface.

Rotation of the second connector portion 403 may also cause the second guide elements 439 to engage and/or contact at least a portion of the inward facing surface of the hole formed in the compartment by the self-drilling elements 435. For example, in instances where the second guide elements 439 are male threads (e.g., self-tapping threads), such threads may create corresponding female threads in the inward facing surface of the hole, e.g., during or after formation of the hole by the self-drilling elements 435.

The second connector portion (and, more particularly, the second guide elements 439) may thus be configured to form and engage with corresponding threads on the inward facing surface of a hole through a wall, bottom, or lid of a compartment, thereby coupling the second connector portion 403 to the compartment. The second connector portion (and, in particular, the second guide elements 439) may also be configured to urge the first connector portion 401 against an outer surface of the compartment (e.g., an outer surface of wall 251) that is around the hole.

The second connector portion 403 may also include a handle. The handle may be configured to help a user to grip and rotate the second connector portion 403 during its installation into a compartment. The type and nature of the handle is not limited, provided it can facilitate the rotation of the second connector portion 403 about an axis extending through and parallel to the first passageway 429. With that in mind, the embodiment of FIGS. 4A-4K depict one example of a connector unit that includes a knurled handle 441 that is integral with or coupled to an intermediate portion of the second body 427, extends around the circumference of the second body 427, and is located proximal to the second guide elements 439.

The use of knurled handle 441 is of course for the sake of example only, and it should be understood that suitable handle may be used, and that handle 441 (or another handle) may be positioned at suitable location. Without limitation, in some embodiments the second connector portion 403 includes a handle that is coupled with or integral to an intermediate portion of second body 427, such that the handle is disposed outside a compartment when the second connector portion 403 is in an installed position.

The second connector portion 403 further includes one or more abutment surfaces 443. The abutment surface 443 is generally configured to abut against a corresponding engagement surface 485 of the fourth connector element 407 when the fourth connector element is in an installed position, as will be further described below. That concept is best shown in FIG. 4C, which depicts abutment surface 443 abutting (e.g. contacting) engagement surface 485 of the fourth connector portion 407 when the fourth connector portion is in an installed position.

The second connector portion 403 further includes at least one proximal opening formed in a wall 433 of the second body 427. In general, the proximal opening is configured to fluidly couple to an outlet port, so as to provide at least a portion of the outlet passageway 413 for the removal of gas (e.g., ozone) from a compartment. That concept is shown in FIGS. 4C and 4E, which illustrate an embodiment in which a plurality of proximal openings 445 are formed through the wall 433, wherein at least one of the proximal openings is in fluid communication with an outlet port 457 on the third connector portion 405.

Of course, the (dual channel) connector units described herein may include greater or fewer proximal holes. When more than one proximal hole is used, all or less than all of such proximal holes may be in fluid communication with an outlet port. That concept is shown in FIG. 4G, which depicts four proximal openings 445 in the second body 427. As shown in FIG. 4C, some the proximal opening(s) 445 are fluidly coupled to outlet port 457, e.g., via a circumferential gap between an inner surface of the second body portion 403 and an outer surface of the third body portion 405.

The location and configuration of the proximal opening(s) formed in the second body 427 is not particularly limited, provided that it is (or they are) positioned such that it remains (or they remain) on the outside of a compartment when all elements of the connector unit 400 are in an installed position, and provided that one or more than one proximal opening is in fluid communication with an outlet port and at least a portion of an outlet passageway that is present between the second connector portion 403 and the fourth connector portion 409. Put in other terms, the second connector portion 403 may include at least one proximal opening 445 that fluidly couples at least a portion of an outlet passageway 413 that is present between the second connector portion and the fourth connector portion to one or more outlet ports.

It is noted that in the embodiment of FIGS. 4A-4K, outlet port 457 and the third body 463 are depicted as components that are separate from the second connector portion 403. In such instances it should be understood that the outlet port 457 and third body 463 may be integral with or coupled to the third connector portion 405. As shown in FIGS. 4C and 4E for example, the third connector portion 405 may comprise the third body 463 and the outlet port 457. In the illustrated embodiment, the third body 463 has a hollow tubular shape with an inside diameter ID3 that is larger than the outside diameter OD2 of a proximal portion of the second connector portion 403.

The third body 463 may thus be configured such that it may slide over a proximal portion of the second connector portion 403, e.g., until a distal facing surface (not labeled) thereof abuts a proximal facing surface of a portion of the second connector portion, e.g., a proximal facing surface (not labeled) of handle 441. Put in other terms, the third body 463 may be in the form of a collar having an outer wall and an opening, wherein the collar is configured to be disposed around a proximal end P2 of the second connector portion 403.

The third body 463 may also include an outlet opening 459 that is fluidly coupled to outlet port 457, which is integral with or coupled to third body 463 in suitable manner. As best shown in FIG. 4C, when the third connector portion is in an installed position (e.g., after third body 463 is slid over a proximal portion of the second connector portion 403 such that a distal face of the third body 463 abuts a proximal face of the handle 435 of the second connector portion 403), the outlet opening 459 may be aligned with one or more of the proximal openings 445 in the second body 427.

Alternatively or additionally, one, more than one, or all of the proximal openings 445 may be in fluid communication with the outlet port opening 459, regardless of whether they are aligned with the outlet port opening or not. In that regard, one or more spacer elements 465 may be disposed within the opening in the third body 463, e.g., as shown in FIGS. 4E and 4J. The spacer elements 465 may be laterally spaced from one another, and may be generally configured to abut with a portion of an outer surface of the second body 427. In addition, the spacer elements 465 may be configured such that a gap is maintained between them, and also between an inward facing surface 467 of the third body 463 and an outward facing surface 434 of a proximal portion of the wall 33 of the second connector portion 403. Put in other terms, the spacer elements 465 may facilitate the maintenance of a circumferential gap between the inward facing surface 467 the outward facing surface 434, wherein the circumferential gap may form part of the outlet passageway 413 for the removal of gas (e.g., ozone) from a compartment.

Although not shown in the figures, in some embodiments the third connector portion 405 may be omitted. In such embodiments the third body 463 and outlet port may be integral with or otherwise coupled to second connector portion 403 in suitable manner. For example, the outlet port 457 and third body 463 may be mechanically coupled to the second connector portion 403, e.g., with one or more adhesives, mechanical fasteners, welds, interference fittings press fittings, combinations thereof, and the like. In such instances, one or more spacer elements may be disposed between the inward facing surface of the third body 463 and the outward facing surface 434 so as to maintain a circumferential gap between such elements, as previously described. Alternatively or additionally, the outlet port 457 and third body may be integral with the second connector portion 403, in which case they may be configured to maintain the circumferential gap in suitable manner.

In some embodiments the connector unit 400 may include an optional first locking portion 409. When used, the first locking portion 409 is configured to fix (i.e., lock) the position of the first connector portion 401 relative to the second connector portion 403, e.g., once the second connector portion 403 is in an installed position. In addition, in some embodiments the first locking portion 409 may also serve to further urge and/or secure the first connector portion 401 against and/or to an outside surface of the compartment, such as the outside of a wall 251 of a compartment as shown in FIG. 4C.

FIG. 4E illustrates one example of a connector unit 400 that includes an optional first locking element 409. In the illustrated embodiment, first locking element 409 is in the form of a threaded nut that is includes an opening 469 and threads 471 on an inward facing surface thereof. The threads 471 are configured to engage with the second guide elements 439 (e.g., threads) on an outer surface of the second body 427. That is, threads 471 may threadably coupled to second guide elements 439. Prior to insertion of the second connector portion 403 into the opening 417, first locking element may be positioned relatively close to the proximal end P2 of the second body. This may be accomplished, for example, by rotating the first locking element 409 relative to the second connector portion 403 while the threads 471 are engaged with the second guide elements 439.

Following insertion of the second connector portion 403 into the opening 417, the second connector portion 403 may be rotated to form a hole in a portion of a compartment (e.g., wall 251). Subsequently (e.g., when the second connector portion is in an installed position), the first locking element 409 may be rotated about an axis extending through and parallel to the second body 427, so as to draw the first locking element 409 towards the distal end D2 of the second connector portion 403 until a surface of the first locking element 409 is adjacent to and/or in contact with a portion of the outward facing surface 423 of the first connector portion 401. Once the first locking element 409 is so positioned, movement of the first connector portion 401 relative to the second connector portion 403 may be hindered and/or prevented. In that way, first locking element 409 may "lock" the position of the first connector portion 401 relative to the second connector portion 403.

Figure 4H:
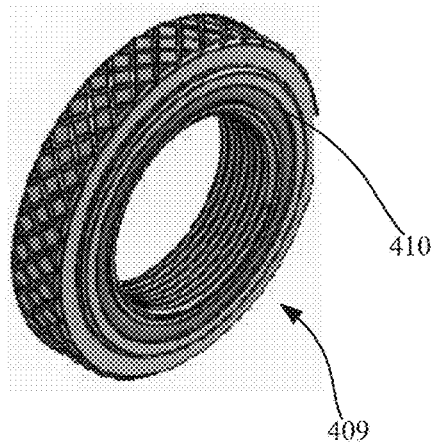
FIGS. 4H and 4I are perspective views of the distal and proximal sides of an optional locking element consistent with the present disclosure.
Figure 4I:
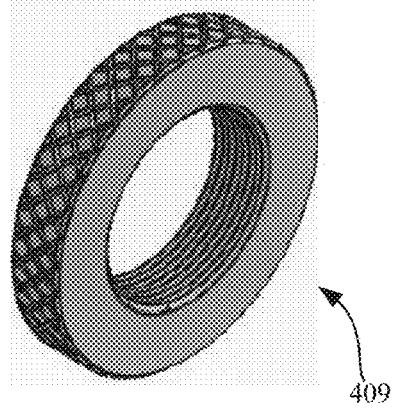
Figure 4J:
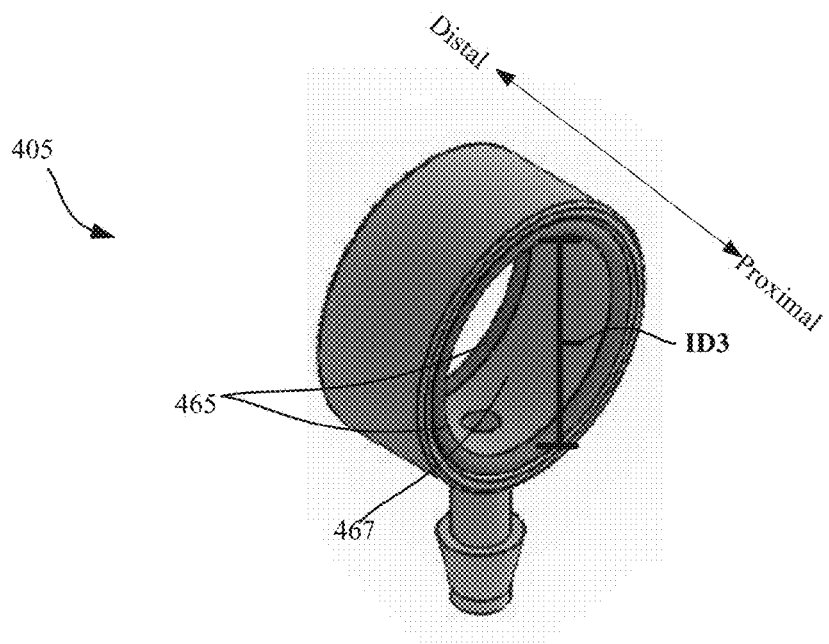
FIG. 4J is a perspective view of a third connector portion consistent with the present disclosure

FIGS. 4H and 4I show the distal and proximal ends, respectively, of one example of a first locking element 409 consistent with the present disclosure. As shown, the first locking element 409 may further include a sealing element 410 disposed on or in proximity to the radial edge of the distal end of the locking element 409. In general, the sealing member (e.g., an O-ring) may be configured to facilitate sealing of the distal end of the locking element 409 against a proximal surface of the first connector portion 401, e.g., to form a gas tight seal.

In some embodiments the connector units described herein may include multiple locking elements. As one example of that concept reference is made to FIGS. 6A and 6B, Such FIGS. depict a connector unit 400' that is substantially similar to connector unit 400, except that it includes both a first locking element 409 and a second locking element 409'.

Similar to connector unit 400, installation of the connector unit 400' may begin by coupling first connector portion 401 to a portion (e.g., wall 251) of a compartment. First locking element 409 may be moved (or may have been previously moved) to a proximal position along the outside surface of the distal portion of the second connector portion 403, as previously described. The distal end D2 of the second connector portion 403 may be inserted into an opening in the first connector portion 401, and the second connector portion 403 may be rotated to cause self-drilling elements 435 to form a hole in the (e.g., wall 251) of the compartment.

Figure 6A:
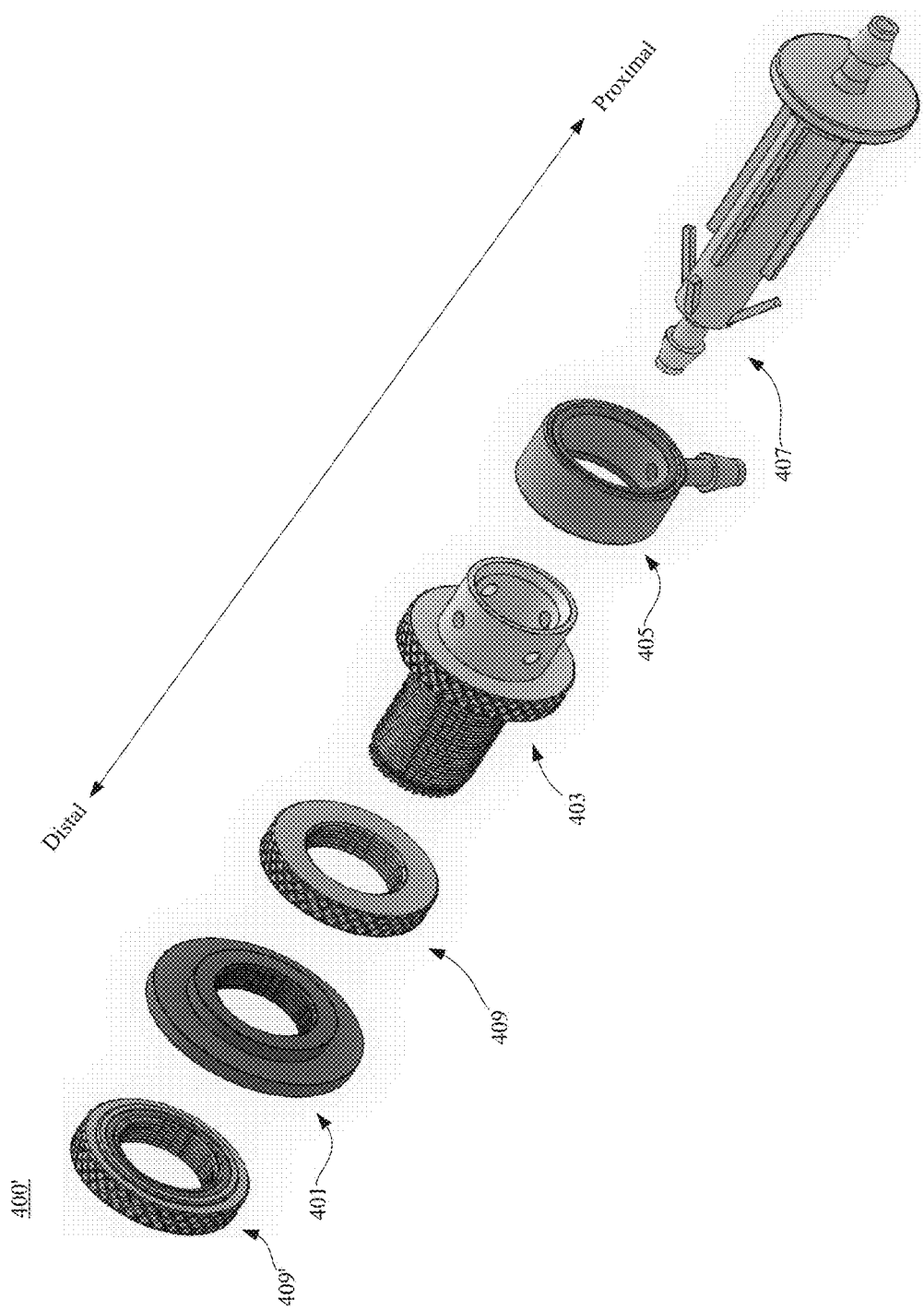
FIG. 6A is a perspective exploded view of another double wall connector unit consistent with the present disclosure.
Figure 6B:
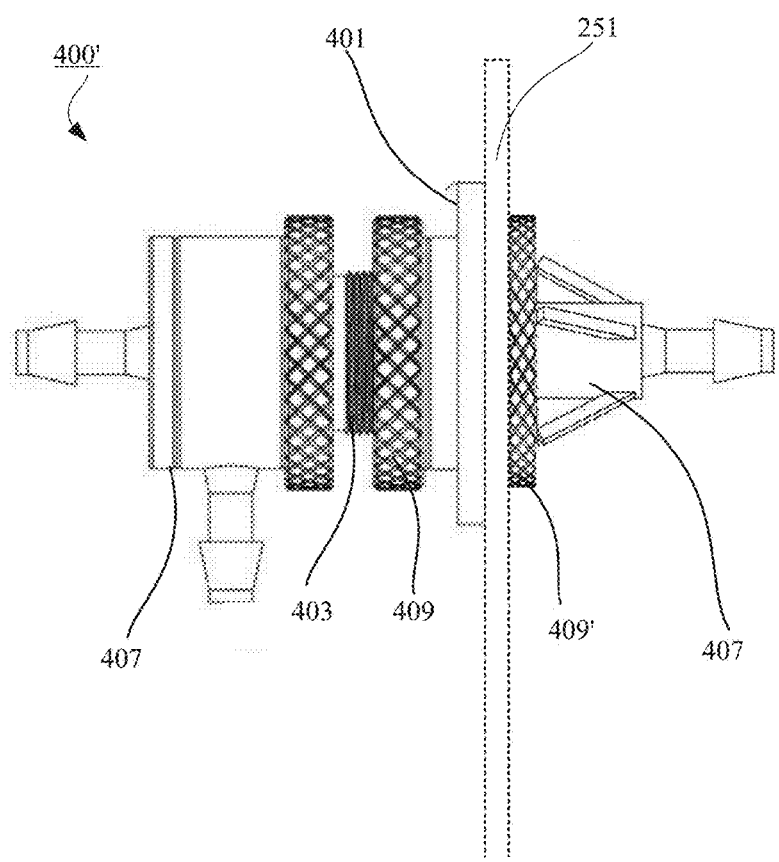
FIG. 6B is a side view of the double wall connector unit of FIG. 6A.

In the embodiment of FIGS. 6A and 6B the second connector portion 403 may be configured such that rotation of the second connector portion 403 eventually causes the distal end D2 thereof to protrude into the compartment. To accomplish this, the length of the distal end D2 of the second connector portion may be configured such that it is greater than a thickness of the wall, bottom, or lid of a compartment. That concept is shown in FIG. 6B, which depicts connector unit 400' as installed through a wall 251 of a compartment.

In the embodiment of FIGS. 6A and 6B the second locking element 409' is configured in substantially the same manner as the first locking element 409. As a result, the second locking element 409' may include an opening having an inward facing surface with threads or other guide elements that are configured to engage second guide elements 439.

In instances where the second guide elements (on an outward facing surface of a wall of the second connector portion 403) are threads, the second locking element 409' may (like the first locking element 409) include corresponding threads. In such instances, the threads of the second locking element 409' may engage with the second guide elements 439, such that rotation of the second locking element 409' draws it along the outside of second body 427, e.g., until the second locking element 409' abuts and/or is in contact with an inward facing surface of the compartment (e.g., and inward facing surface of wall 251. That concept is shown in FIG. 6B, which shows connector unit 400' installed in a wall 251 of a compartment, with first and second locking elements 409, 409' disposed on outer and inward facing sides of the wall 251. An optional sealing element 410 may also be disposed on one side of the second locking element 409' to facilitate the formation of a seal with an inward facing surface of the compartment, e.g., in the same manner shown in FIG. 4H.

Returning to FIGS. 4A-4K, the connector unit 400 further includes a fourth connector portion 407. In general, the fourth connector portion 407 is configured to be inserted into or otherwise retained within the second connector portion 403, and to provide the inlet passageway 411 for the supply of gas (e.g., ozone) into a compartment. In addition, the fourth connector portion is configured to provide a portion of the outlet passageway 413 for the removal of gas (e.g., ozone) from the compartment.

Figure 4K:
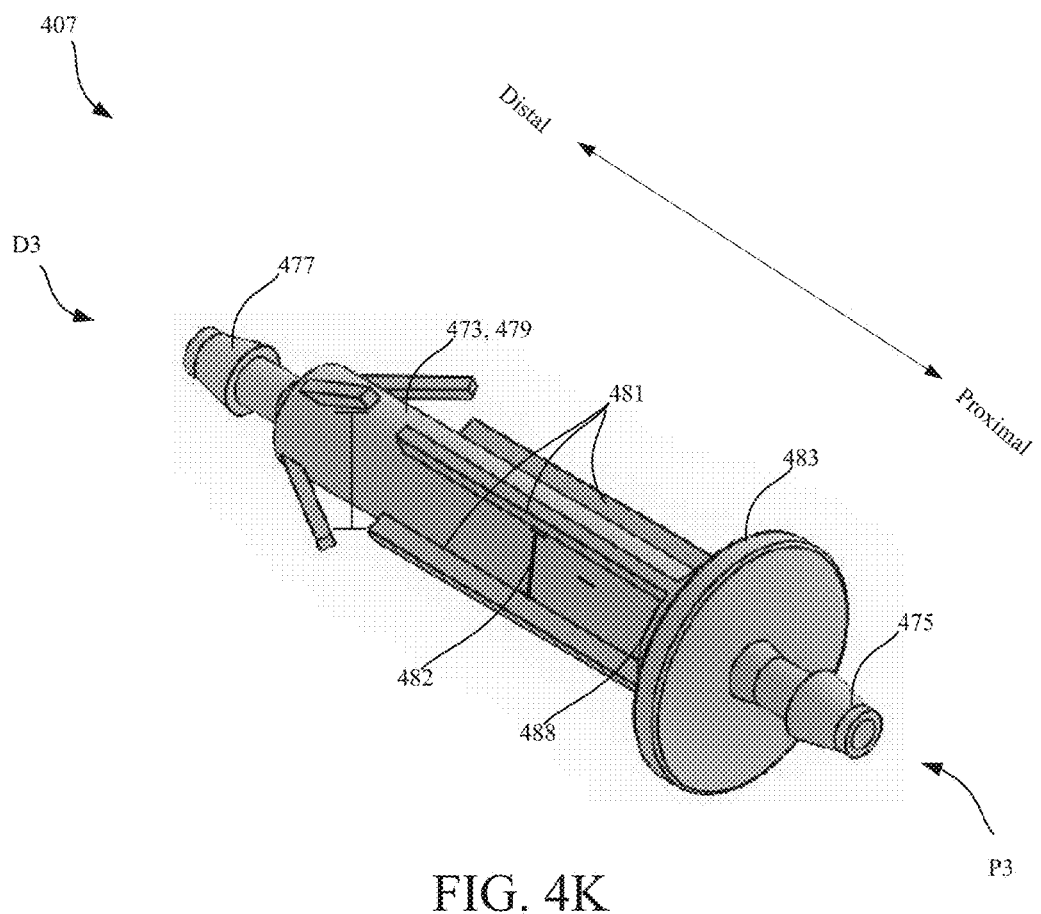
FIG. 4K is a perspective view of a fourth connector portion consistent with the present disclosure.

FIG. 4K depicts one example of a fourth connector portion 407 consistent with the present disclosure. As shown, the fourth connector portion includes a third body 473 having a proximal end P3 and a distal end D3. A first inlet connector 475 is disposed at the proximal end P3, a second inlet connector 477 is disposed at the distal end D3, and a flange 483 is disposed near the proximal end P3. As best shown in FIG. 4C, the inlet passageway 411 is formed through the fourth connector portion and extends between first and second inlet connectors 475, 477. Thus, a proximal end 489 of the inlet passageway 411 is present within the first inlet connector 475, and a distal end 491 of the inlet passageway is present within the second inlet connector. As may be appreciated, a gas supply (e.g., ozone device 101), may be coupled to the first inlet connector 475. In such instances the gas supply may be used to provide gas (e.g., ozone) to the first inlet connector 475 for conveyance through the inlet passageway 411 and to the second inlet connector 477.

As best shown in FIGS. 4C and 4E, the third body 473 has an outer diameter OD3 (not labeled) that is smaller than the inner diameter ID2 of the proximal portion of the second connector portion 403. As a result, a distal portion of the third body 473 (e.g., distal of the flange 483) may be inserted into the first passageway 429 of the second connector portion 403. The distal portion of the third body 473 may be configured such that when it is fully inserted into the first passageway 429, the second inlet connector 477 extends past the circumferential edge 437 of the second connector portion 403. In that position, an engagement surface 485 of the fourth connector portion 407 (e.g., a portion of the flange 483) may abut a corresponding abutment surface 443 of the second connector portion 403. In some embodiments, at least a portion of the flange 483 may also abut and/or contact a portion of the third connector portion 405, e.g., a proximal circumferential edge 468 thereof.

As best shown in FIG. 4C when the fourth connector portion 407 is fully inserted into the first passageway 429, a gap is present between the inner surface 431 of the wall 433 of the second connector portion 403 and the outer surface 479 of the third body 473 of the fourth connector portion 407. That gap forms a portion of an outlet passageway 413 for the removal of gas from a compartment.

In the embodiment of FIGS. 4A-4K the distal end 493 of the outlet passageway 413 is or includes an opening that is present between the outer surface 479 of the third body 473 and the circumferential edge 437 of the second connector portion 403, and the proximal end 495 of the outlet passageway 413 is present in the outlet port 457. From the distal end 493 the outlet passageway 413 extends, via the gap between the inner surface 431 and the outer surface 479, proximally towards the flange 483. Near the flange 483 the outlet passageway extends through one or more proximal openings 445 in the second connector portion 403 and into the circumferential gap between the inward facing surface 467 of the third body 463 and the outward facing surface 434 of the second body 427. The outlet passageway 413 then continues via the gap to outlet opening 459, which is coupled to outlet port 457.

Accordingly, a gas inflow 497 may be supplied from the first inlet connector 475 to the second inlet connector 477 via the inlet passageway 411 and into a compartment. Similarly, a gas outflow 499 may be drawn from a compartment into the distal end 493 of the outlet passageway 413, to the proximal end 495 of the outlet passageway, and ultimately out of the connector unit 400.

To maintain the gap between the inner surface 431 and the outer surface 479, in some embodiments the fourth connector portion may include one or more standoff elements. That concept is shown in FIGS. 4D, 4E, and 4K, which depict fourth connector portion 407 as including a plurality of standoff elements 481. As shown, the each of the standoff elements 481 extends from an outer surface 479 of the third body 473.

The standoff elements 481 are each configured to partially or fully bridge the gap between the inner surface 431 and outer surface 479 when the fourth connector portion 407 is inserted into the first passageway 429 of the second connector portion 403. In such instances a channel 482 may be present between a respective two of the plurality of standoff elements 481. As shown in FIG. 4E, the fourth connector portion 407 may be aligned such that when it is inserted into the first passageway 429, at least one proximal opening 445 in the second connector portion 403 is disposed between two of the standoff elements 481, i.e., such that it is in fluid communication with a channel 488. A gas in gas outflow 499 may then travel from a channel 488 into a proximal opening 445, into the circumferential gap (described above) and then into the outlet opening 459.

As noted above the fourth connector portion 407 includes a flange 483 that abuts at least a portion of the second connector portion 403 when the fourth connector portion 407 is fully inserted therein. In some embodiments, the flange 483 may include a plug 488. The plug 488 may be have an outside diameter OD4 (not shown) that is less than the inside diameter ID2 of the proximal end P2 of the second connector portion 403. Thus when the fourth connector portion 407 is fully inserted into the second connector portion 403, an outward facing surface of the plug 488 may abut and/or contact the inner surface of wall 433, as shown in FIG. 4C. In addition, one or more sealing elements 490 (e.g., O-rings, gaskets, adhesive, including ozone resistant adhesives, polymers, or other sealing elements) may be disposed between the plug 488, flange 483, and the inward facing surface 433, e.g., to provide a gas-tight seal between such elements.

In some embodiments the fourth connector portion 407 may also include one or more retention elements. When used, such retention elements may be configured to facilitate retention of the fourth connector portion 407 within the second connector portion 403. More particularly, in some embodiments the retention elements may be configured to hinder or prevent lateral movement of the fourth connector portion 407 once it is fully inserted into the second connector portion 403. Non-limiting examples of suitable retention elements that may be used include detents, protuberances, other engagement elements, combinations thereof, and the like. With that in mind, FIGS. 4A-4E, 4K, 6A, and 6B depict embodiments in which the fourth connector portion 407 includes retention elements in the form of deformable protrusions 487 (e.g., deformable wings).

As will be appreciated from the figures, the deformable protrusions 487 may be configured to bend, collapse, or otherwise deform in a first direction (e.g., proximally towards first inlet connector 475) from an expanded position into a compressed position. In the expanded position the deformable protrusions 487 may be larger than the inside diameter ID2 of the first passageway 429 in the second connector portion 403. As a result, the deformable protrusions 487 may deform into the compressed position when the fourth connector portion is inserted and urged into the first passageway 429.

The deformable protrusions 487 may remain in the collapsed/compressed position until they are advanced past the distal end of the first passageway 429. When the deformable protrusions 487 are advanced past the distal end of the first passageway 429, they may return to the expanded (e.g., decompressed) position. Thereafter, removal of the fourth connector portion 407 from the first passageway 429 may be hindered and/or prevented by the deformable protrusions 429. Moreover, the deformable protrusions may resist deformation in a second direction (e.g., distally in a direction towards second inlet connector 477.

Figure 5:
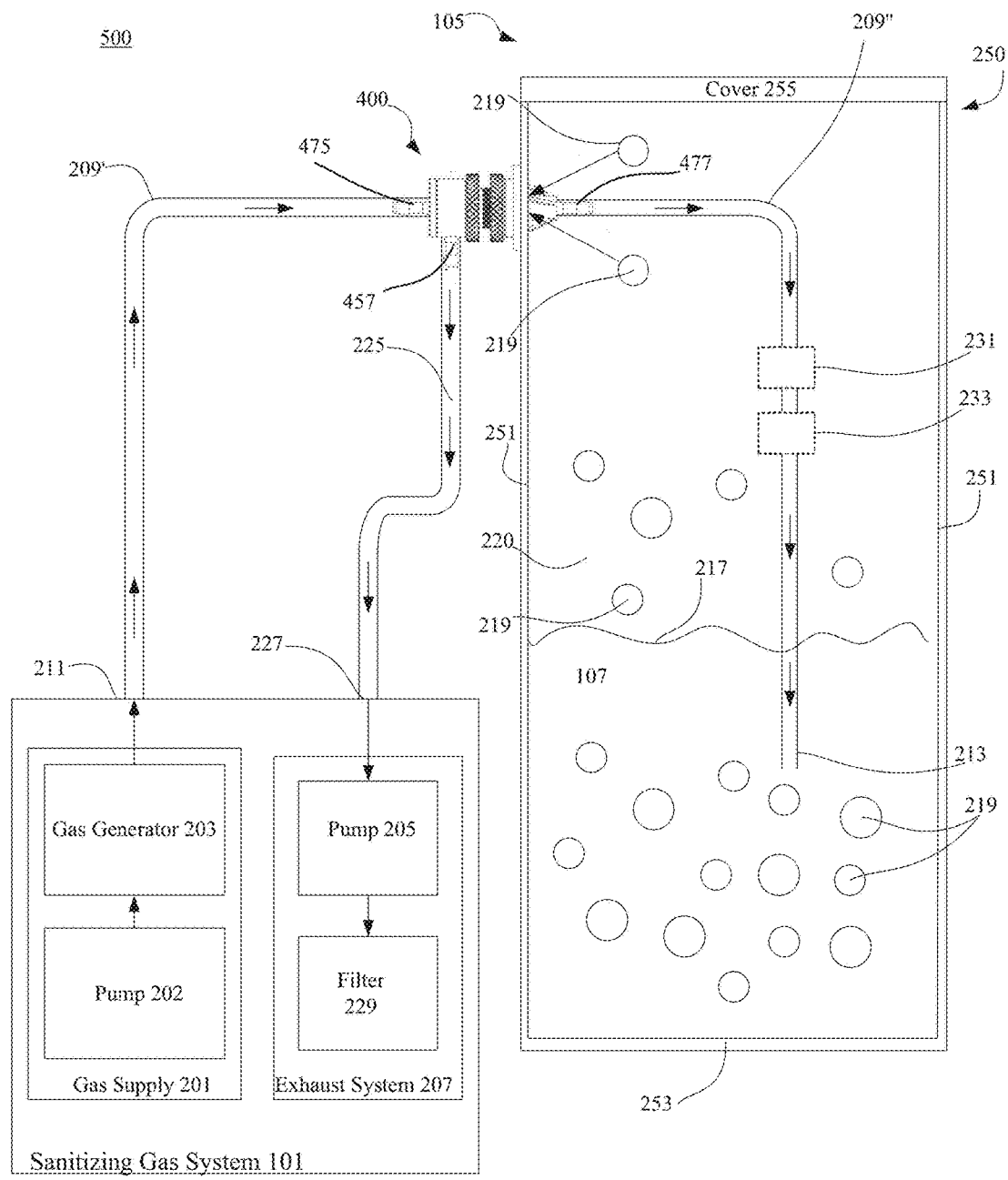
FIG. 5 illustrates an example compartment sanitization system including the double wall connector unit of FIGS. 4A-4K.

FIG. 5 depicts one example of a compartment sanitization system utilizing the connector unit 400 of FIGS. 4A-4K. The nature and function of many of the elements of FIG. 5 are the same as those shown in FIG. 2 and described above, and thus a detailed description of such elements is not reiterated. As shown, system 500 includes an ozone device 101 and a self-drilling, double wall connector unit 400, which in this embodiment is depicted as installed within a wall 251 of a compartment 250.

Installation of the connector unit 400 into wall 251 may be accomplished in suitable manner. For example and consistent with the foregoing description of FIGS. 4A-4K, installation of the connector unit 400 may begin by coupling a first connector portion 401 thereof to the wall 251 (e.g., via an adhesive). A distal end of a second connector portion 403 may be inserted into an opening in the first connector portion 401. The second connector portion 403 may then be rotated to advance the distal end thereof through the opening in the first connector portion, until self-drilling elements on the distal end contact an outer surface of the wall 251. The second connector portion 403 may then continue to be rotated to cause the self-drilling elements to form a hole in the wall 251. In some embodiments at least a portion of the distal end of the second connector portion may be disposed within an interior of the compartment 250 following the formation of the hole.

After the hole is formed a third connector portion 405 may be disposed over the proximal end second connector portion 403. A fourth connector portion 407 may then be inserted into a proximal end of a first passageway extending through the second connector portion. The fourth connector portion 407 may include retaining elements that deform from an expanded to a compressed position while a distal end of the fourth connector portion 407 is inserted into the first passageway in the second connector portion 403. When the fourth connector portion 407 is fully inserted, the retaining elements may return to the expanded position, hindering or preventing retraction of the fourth connector portion 407 through the first passageway. A flange on the fourth connector portion 407 may abut and form a gas tight seal with one or more portions of the proximal end of the second connector portion 403 and the third connector portion 405.

As previously described, an inlet passageway 411 is provisioned in the fourth connector portion and extends between a first inlet connector 475 and a second inlet connector 477. In addition, an outlet passageway 413 is provisioned as previously described, and extends between a distal end of the second connector portion and an outlet connector 457.

As shown in FIG. 5, sanitizing gas system 101 includes a gas supply 201 and an exhaust system 207. The gas supply 201 includes a pump 202 and a gas generator 203, and the exhaust system 207 includes a pump 205 and a filter 229. The gas supply 201 is fluidly coupled to the inlet passageway 411 by a first supply line 209', the distal end of which is coupled to the first inlet connector 475. A second supply line 209" is coupled to the second inlet connector 477. The exhaust system 207 is fluidly coupled to the outlet passageway 413 via return line 225, the distal end of which is coupled to the outlet connector 457.

In operation the gas generator 203 generates sanitizing gas 219 (e.g., ozone). The pump 202 (e.g. an air pump) generates an air flow that causes the sanitizing gas to be conveyed to the first supply line 209', into the inlet passageway 411, and into the second supply line 209". The sanitizing gas 219 exits the distal end 213 of the second supply line 209" to sanitize the interior of the compartment 250 and liquid therein, as described above in connection with FIG. 2. The pump 205 (e.g., a vacuum pump) operates to draw excess sanitizing gas 219 from the interior of the compartment 250 into a distal end 493 of the outlet passageway 413, through the outlet passageway 413, through outlet connector 457, and into return line 225. The excess sanitizing gas 219 may then be conveyed to the filter 229, which may remove the excise sanitizing gas 219 or convert it to another composition. For example where the sanitizing gas 219 is ozone, the filter 229 may be configured to convert at least a portion of the ozone to oxygen.

Figure 7:
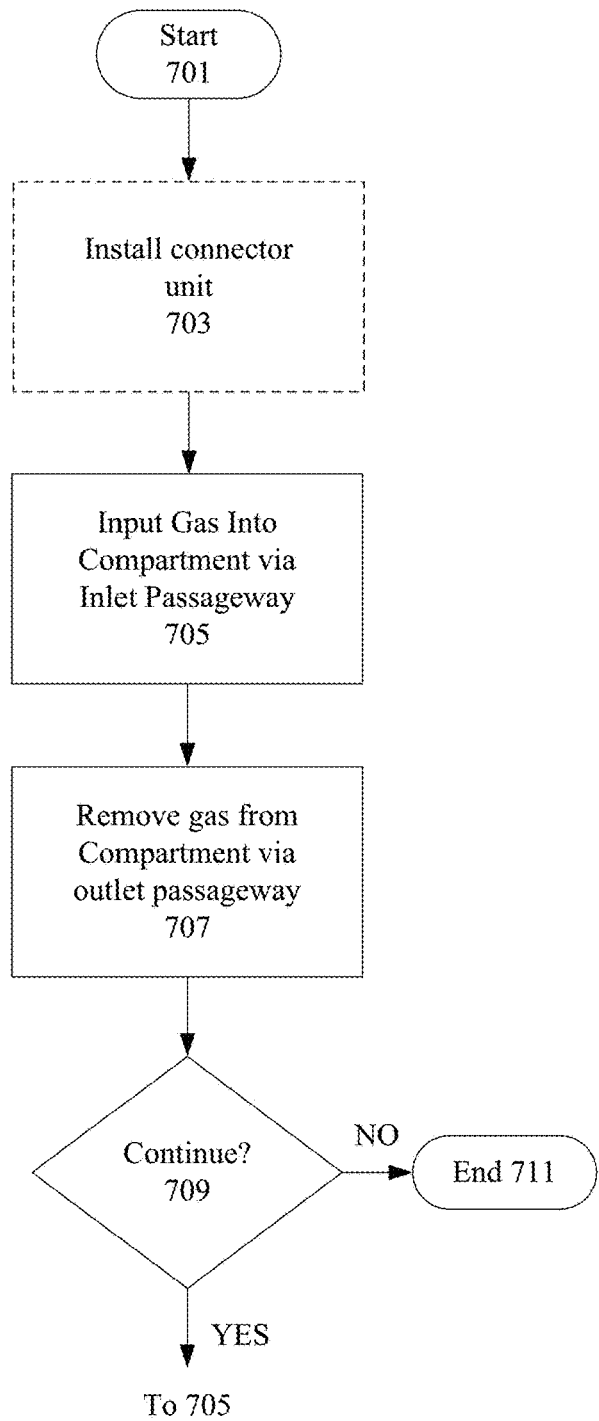
FIG. 7 is a flow chart of example operations of one example of a compartment sanitization method consistent with the present disclosure.

Another aspect of the present disclosure relates to methods for sanitizing a compartment utilizing a dual channel connector unit. In that regard reference is made to FIG. 7, which is a flow chart of example operations of one example of a compartment sanitization method consistent with the present disclosure. As shown, the method 700 begins at block 701. The method may then advance to optional block 703, pursuant to which a dual channel connector unit consistent with the present disclosure may be installed in a portion of a compartment. For example, operations pursuant to block 703 may include installing a double wall connector unit or a self-drilling, double wall connector unit consistent with the present disclosure into a wall, bottom, top, or lid of a compartment, as previously described.

Following the operations of block 703 or if block 703 is omitted (e.g. where a connector unit has been previously installed), the method may proceed to block 705. Pursuant to block 705 a sanitizing gas may be provided into a compartment via an inlet passageway of the connector unit, e.g., as described above. Thus for example, operations pursuant to block 705 may include generating a sanitizing gas with a gas generator, causing the sanitizing gas to flow into a first supply line, into the inlet passageway, into a second supply line, and into the interior of the compartment, as previously described. At least a portion of the sanitizing gas so provided may sanitize the interior of the compartment, including liquid (e.g., water therein).

The method may then advance to block 707, pursuant to which excess sanitizing gas may be removed from the interior of the compartment. Consistent with the foregoing description, operations pursuant to block 707 may include drawing sanitizing gas from the interior of the compartment into a distal opening of the outlet passageway, through the outlet passageway, through an outlet connector, and to a return line. The operations pursuant to block 707 may also include conveying the sanitizing gas to a filter, as discussed above.

Following the operations of block 707 the method may proceed to block 709, pursuant to which a decision may be made as to whether the method is to continue. The outcome of the decision block 709 may be contingent on a sensor signal provided, e.g., by an optional sensor 233 or on some other criteria. In case if the method is to continue it may loop back to block 705. But if not, the method may proceed to block 711 and end.

The following examples pertain to additional non-limiting embodiments of the present disclosure.

Example 1 provides an overall system for supplying a gas inlet and outlet to a compartment, the system comprising, a connector unit with an inlet passageway and an outlet passageway, the inlet passageway comprising a first proximal end and a first distal end and the outlet passageway comprising a second proximal end and a second distal end, wherein at least a portion of the outlet passageway is disposed radially around the inlet passageway; and an exhaust system configured to remove the gas.

Example 2 comprises a system for supplying a gas inlet and outlet of Example 1 further including at least a portion of the outlet passageway is disposed radially around the inlet passageway, such that the gas supply system is configured to fluidly couple to the inlet passageway and the exhaust system is configured to fluidly couple to the outlet passageway.

Example 3 comprises a system for supplying a gas inlet and outlet of Example 1 further including the connector unit configured to be installed into and span a portion of a compartment such that the first and second proximal ends are located outside the compartment and the first and second distal ends are located inside the compartment when the connector unit is installed.

Example 4 comprises a system for supplying a gas inlet and outlets of Example 1 further including the gas supply system configured to supply the gas to an inside of the compartment via the inlet passageway and the exhaust system is configured to remove the gas from the inside of the compartment via the outlet passageway.

Example 5 provides an over description of a self-drilling connector unit configured to traverse a wall of a compartment, wherein: the self-drilling connector unit comprises a first wall and a second wall, the first wall comprises an inlet passageway to provide gas to an interior of the compartment, the inlet passageway extending from a proximal end to a distal end of the self-drilling connector unit; and, the self-drilling connector unit further comprises an outlet passageway between the first wall and the second wall, the outlet passageway to remove ozone gas from the interior of the compartment.

The terms and expressions which have been employed herein are used as terms of description and not of limitation, and there is no intention, in the use of such terms and expressions, of excluding equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A connector unit comprising:
    an inlet passageway and an outlet passageway, the inlet passageway comprising a first proximal end and a first distal end and the outlet passageway comprising a second proximal end and a second distal end;
    a second connector portion comprising a first body comprising a first wall having a first inward facing surface, a first outward facing surface, and an end surface, the first body further comprising a first passageway; and
    a fourth connector portion configured to be inserted into the first passageway, the fourth connector portion comprising a second body comprising a second wall having a second inward facing surface, a second outward facing surface;
wherein:
    at least a portion of the inlet passageway is disposed in the fourth connector portion;
    at least a portion of the outlet passageway is disposed between the first inward facing surface and the second outward facing surface, such that at least a portion of the outlet passageway is disposed radially around the inlet passageway;
    the second connector portion further comprises self drilling elements that are integral with or coupled to the end surface of the first wall; and
    the connector unit is configured to be installed into and span a portion of a compartment such that the first and second proximal ends are located outside the compartment and the first and second distal ends are located inside the compartment when the connector unit is installed.

2. The connector unit of claim 1, further comprising:
    a first inlet connector coupled to the first proximal end; and
    a second inlet connector coupled to the first distal end.

3. The connector unit of claim 2, further comprising an outlet connector configured to couple to the second proximal end.

4. The connector unit of claim 2, wherein the second inlet connector comprises said first distal end, and the second distal end is located proximal to the first distal end.

5. The connector unit of claim 1, wherein the second distal end is located proximal to the first distal end.

6. The connector unit of claim 1, wherein said self drilling elements comprise teeth, blades, or a combination thereof.

7. The connector unit of claim 1, wherein:
    when the fourth connector portion is inserted into the first passageway, a gap is present between the second outward facing surface and the first inward facing surface; and
    said gap defines at least a portion of the outlet passageway.

8. The connector unit of claim 7, further comprising at least one standoff element extending from the second outward facing surface, the at least one standoff element to maintain the gap between the second outward facing surface and the first inward facing surface when the fourth connector portion is inserted in the first passageway.

9. The connector unit of claim 7, wherein:
the fourth connector portion further comprises a flange;
the second connector portion comprises an abutment surface; and
an engagement surface of the flange is configured to abut the abutment surface when the fourth connector portion is inserted into the first passageway.

10. The connector unit of claim 9, further comprising at least one sealing element, wherein:
said flange further comprises a plug;
when the fourth connector portion is inserted into the first passageway:
the plug is disposed within a proximal end of the first passageway; and
the at least one sealing element is disposed between the first inward facing surface and at least a portion of said plug, so as to form a gas-tight seal.

11. The connector unit of claim 7, wherein:
the first passageway comprises a proximal opening and a distal opening;
the self-drilling elements are disposed about the distal opening.

12. The connector unit of claim 7, further comprising a first connector portion that is configured to couple to a portion of the compartment, wherein:
the first connector portion comprises an opening; and
the second connector portion is configured to be inserted into the opening of the first connector portion.

13. The connector unit of claim 12, wherein:
the first connector portion comprises first guide elements within the opening;
the second wall comprises a distal portion and a proximal portion;
second guide elements are formed on the second outward facing surface proximate the distal portion of the second wall; and
the second guide elements and first guide elements are configured to draw the distal portion of the second wall into the opening of the first connector portion.

14. The connector unit of claim 13, wherein:
the first guide elements are first threads; and
the second guide elements are second threads configured to threadably engage with the first threads to draw the second body into the opening of the first connector portion when the second connector portion is rotated about an axis that is parallel to and extends through the first passageway.

15. The connector unit of claim 13, further comprising at least one locking element configured to be disposed on the outward facing surface of the second wall, wherein the at least one locking element is configured to lock the relative position of the first connector portion and the second connector portion.

16. The connector unit of claim 15, wherein the second connector portion comprises a handle, and the at least one locking element is between the handle and the first connector portion.

17. The connector unit of claim 15, wherein:
the at least one locking element comprises a first locking element and a second locking element;
the first locking element configured to be disposed distally from the first connector portion; and
the second locking element is configured to be disposed proximally from the first connector portion.

18. The connector unit of claim 7, wherein:
the second wall comprises a distal portion and a proximal portion; and
at least one proximal hole is present through the proximal portion of the second wall, the at least one proximal hole forming at least a portion of the outlet passageway.

19. The connector unit of claim 18, further comprising a third connector portion comprising a collar defining an opening, the collar comprising a proximal edge, at least one spacer element disposed within the opening, and at least one outlet opening; wherein:
the collar is configured to be disposed over the proximal portion of the second wall;
when the collar is disposed over the proximal portion of the second wall, the at least one spacer element is disposed between an inward facing surface of the collar and the second outward facing surface, such that a circumferential gap is present between the inward facing surface of the collar and the second outward facing surface, the circumferential gap fluidly coupling the at least one proximal hole with the at least one outlet opening; and
the circumferential gap and the outlet opening form at least a portion of said outlet passageway.

20. The connector unit of claim 19, wherein:
the collar of the third connector portion comprises a proximal circumferential edge; and
when the collar is disposed over the proximal portion of the second wall and the fourth connector portion is inserted into the first passageway, at least a portion of the flange of the fourth connector portion abuts the proximal circumferential edge.

\* \* \* \* \*